United States Patent [19]

Handte et al.

[11] 4,442,294

[45] Apr. 10, 1984

[54] PROCESS FOR THE PREPARATION OF HALO-2-MERCAPTOBENZOXAZOLES

[75] Inventors: Reinhard Handte, Hofheim am Taunus; Jürgen Sander, Kelkheim; Thomas Tammer, Hofheim am Taunus, all of Fed. Rep. of Germany

[73] Assignee: Hoechst Aktiengesellschaft, Frankfurt am Main, Fed. Rep. of Germany

[21] Appl. No.: 383,209

[22] Filed: May 28, 1982

[30] Foreign Application Priority Data

Jun. 1, 1981 [DE] Fed. Rep. of Germany ....... 3121675

[51] Int. Cl.$^3$ ............................................ C07D 263/58
[52] U.S. Cl. .................................................... 548/221
[58] Field of Search ......................................... 548/221

[56] References Cited

U.S. PATENT DOCUMENTS 4,130,413  12/1978  Handte et al. ........................... 71/90

OTHER PUBLICATIONS

Katz et al. (I), Journal of Org. Chem. 19, 758–766 (1954), "Benzoxazole Derivatives, I2-Mercaptobenzoxazoles".

Kirk–Othmer, "Encyclopedia of Chemical Technology", vol. 22, 419–429, (1970), John Wiley & Sons, Inc.
Kalckhoff, F. A., Chem. Ber. 16, 1825–1833, (1883).
Deck, J. F. et al., J.A.C.S., 55, 4989–4991, (1933), "Synthesis of Heterocyclic Compounds by Means of Isotheourea Ethers".
Katz & Cohen (II), Jr. of Org. Chem. 19, (1954), 767–772, Benzoxazole Der. II, 2-Dialkylamino Alkylmercaptobenzoxazole".
Zenner et al., Chem. Ber., 89, (1956), 1012–1016.
Nagano et al., J.A.C.S., 75, 2770–2771, (1952), "Preparation of Certain Derivatives of Benzoxazoles".
Desai et al., J.C.S., (1934), 1186–1190, "The Unsaturation and Tautomeric Mobility of Heterocyclic Comps., Part V Benzoxazoles".

Primary Examiner—Donald G. Daus
Assistant Examiner—S. A. Gibson
Attorney, Agent, or Firm—Curtis, Morris & Safford

[57] ABSTRACT

Preparation of 5- and 6-halo-2-mercaptobenzoxazoles or the sodium and potassium salts thereof by reaction of corresponding 4- or 5-halo-2-aminophenols with sodium or potassium lower alkyl xanthates in heterogeneous phase.

5 Claims, No Drawings

PROCESS FOR THE PREPARATION OF HALO-2-MERCAPTOBENZOXAZOLES

Subject of the invention is a process for the preparation of halo-2-mercaptobenzoxazoles of the formula I

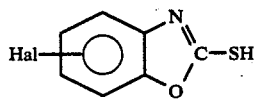

in which Hal is halogen in 5- or 6-position, especially fluorine, chlorine or bromine.

2-Mercaptobenzoxazole was first described in Berichte 9 (1876), page 465. Subsequently, various authors have dealt with the preparation and the reactions of (optionally substituted) 2-mercaptobenzoxazoles (cf. Ber. 16 (1883) 1825; JACS 55 (1933) 4989; J. chem. Soc. 1934, 1186; JACS 75 (1952) 2770-71; J. org. Chem. 19 (1954), 758; Ber. 89 (1956), 1014 and Org. Synth. 30, 56).

Until now 2-mercaptobenzoxazoles and especially the halo-derivatives thereof have not been of particular scientific or industrial interest. Most of the preparation processes hitherto known produce the 2-mercaptobenzoxazoles with medium to poor yields and have the disadvantage of requiring the use of carbon disulfide at elevated temperatures. Katz and Cohen (J. org. Chem. 19, (1954) 758) proved for the first time that 2-mercaptobenzoxazoles can be obtained with good yields by reacting potassium methyl xanthate freshly prepared from methanol, potassium hydroxide and carbon disulfide with substituted 2-aminophenols. According to the authors, however, 6-chloro-2-mercaptobenzoxazole is obtained with very poor yield of only 48% of theory, and for the corresponding 5-chloro derivative no yields whatsoever are indicated.

Recently, the 5- and 6-halo-2-mercaptobenzoxazoles have become of interest as starting substances for the manufacture of important intermediates and final products. Thus, for example, they can be converted by chlorination to the corresponding 2-chlorobenzoxazoles or by alkylation and oxidation to the corresponding 2-alkylsulfonyl- or -sulfinylbenzoxazoles, which in turn yield herbicides of excellent efficiency as described in U.S. Pat. No. 4,130,413 or European Pat. No. 18,080, to which express reference is made herewith.

It was therefore the object of the invention to provide an industrial synthesis of the 5- and 6-halo-2-mercaptobenzoxazoles which is economic, free from the cited disadvantages, unobjectionable as to safety, and environmentally acceptable.

This object is achieved by means of the process of the invention which comprises reacting the corresponding 4- or 5-halo-2-aminophenols with alkali metal lower alkyl xanthates in heterogeneous phase.

The known processes for the preparation of (substituted) mercaptobenzoxazoles from 2-aminophenols and xanthates have in common that the reaction is carried out in solution, generally using ethanol, optionally with a small amount of water (less than 20%). It is therefore surprising to observe that in order to obtain high yields those reaction media or mixtures thereof are suitable in which one of the reactants and optionally the mercaptide formed as primary final product are substantially insoluble or soluble to a small extent only.

Suitable reaction media for the process of the invention are aprotic solvents, especially aromatic hydrocarbons such as xylene, chlorobenzene or dichlorobenzene. Water, too, can be used for the reaction, which is especially surprising in view of the relative instability of xanthates in water at elevated temperatures.

For the cyclization with chloro-aminophenol, xanthates freshly prepared (from alcohol, aqueous alkali and $CS_2$) or industrial-grade xanthates may be used. The latter, especially sodium or potassium (methyl to hexyl) xanthates, are basic chemicals applied on a large scale as flotation auxiliaries. Suitable commercial xanthates to be advantageously used in the reaction are for example sodium or potassium methyl xanthate, sodium or potassium propyl and isopropyl xanthate, and sodium or potassium isobutyl xanthate.

The reaction is generally carried out at temperatures above 50°, preferably above 80° C. At about 80° C. of inner temperature the reaction starts spontaneously and then proceeds at boiling temperature of the alcohol which is released as by-product of the xanthate decomposition. However, to complete the reaction the inner temperature can be raised by distilling off the alcohol to the boiling temperature of the reaction medium and preferably to about 120° C. When using low-boiling reaction media such as toluene or water the reaction may be carried out in a sealed vessel and at pressures of up to 10 bar.

The hydrogen sulfide formed in the reaction is continuously degassed from the reaction medium and externally absorbed.

The following Examples illustrate the invention without limiting its scope thereto.

EXAMPLE 1

6-Chloro-2-mercaptobenzoxazole 143.6 g (1 mol) of 5-chloro-2-aminophenol, 164 g (1.02 mols) of sodium methyl xanthate (90% strength) and 500 ml of water were introduced into a 1 liter flask equipped with stirrer, thermometer and reflux condenser. The reaction mixture (the chloro-aminophenol remained undissolved) was warmed with stirring, from 80° C. on vigorous hydrogen sulfide development occured. After about 1 hour the reaction was essentially complete, but stirring with reflux was continued for a further 2 hours. The resulting black reaction solution was cooled, and acidified with 70 g of 85% phosphoric acid. The precipitate was suction-filtered, washed thoroughly with water and subsequently dried at about 80° C. under reduced pressure. After drying, 180.5 g (97.3% of th.) of 6-chloro-2-mercaptobenzoxazole having a melting point of 221°-223° C. were obtained. (The literature gives a m.p. of 224°-225° C. after recrystallization from water/isopropanol, J. org. Chem. 19, 758). According to gas chromatography, the purity degree of the product was higher than 98%.

EXAMPLE 2

6-Chloro-2-mercaptobenzoxazole

Operations were as described in Example 1, however, instead of sodium methyl xanthate, 213.1 g (1.02 mols) of potassium isobutyl xanthate were used. After work-up, 178 g (96% of th.) of 6-chloro-2-mercaptobenzoxazole having a melting point of 222°-223° C. were obtained having a purity of more than 98% according to GC.

EXAMPLE 3

5-Chloro-2-mercaptobenzoxazole

With the use of the apparatus described in Example 1, 143.6 g (1 mol) of 4-chloro-2-aminophenol and 181.3 g (1.02 mols) of potassium methyl xanthate (90%) in 500 ml of water were refluxed. The reaction was complete within 3 hours. The dark reaction solution was acidified with concentrated hydrochloric acid, the precipitate was suction-filtered and washed neutral with water. After drying in vacuo at 80° C., 179 g (96.7% of th.) of 5-chloro-2-mercaptobenzoxazole having a melting point of 269°–271° C. were obtained.

EXAMPLE 4

6-Chloro-2-mercaptobenzoxazole and the sodium salt thereof

In analogy to Example 1, 143.6 g (1 mol) of 5-chloro-2-aminophenol and 164 g (1.02 mols) of sodium methyl xanthate in 600 ml of 1,2-dichlorobenzene were reacted with heating and stirring. At an inner temperature of 80°–82° C., vigorous hydrogen sulfide development occured and a precipitate of sodium mercaptide formed. After 5 hours the batch was partially distilled, cooled, suction-filtered and dried at 80° C. in vacuo. 209 g of a solid matter consisting nearly exclusively of sodium salt of 6-chloro-2-mercaptobenzoxazole resulted. In order to obtain the free mercapto compound the salt was dissolved in 1,200 ml of water and the solution adjusted to pH 1 with 2 N sulfuric acid. The solid precipitate was suction-filtered, washed thoroughly with water and dried at 80° C. in vacuo. After drying, 178 g (96% of th.) of 6-chloro-2-mercaptobenzoxazole having a melting point of 223°–225° C. were obtained.

EXAMPLE 5

Operations were as indicated in Example 4; however, instead of 1,2-dichlorobenzene, chlorobenzene was used as medium. As xanthate, 181,3 g (1.02 mols) of potassium methyl xanthate were used. After a reaction time of 5 hours at 90° C. the batch was partially distilled, cooled and suction-filtered. The solid product was washed with 500 ml of chlorobenzene and dried at 80° C. in vacuo. After drying, 226 g of a solid matter consisting nearly exclusively of the potassium salt of 6-chloro-2-mercaptobenzoxazole were obtained. The mercapto compound was set free as described in Example 4. After drying, 179 g (96.5% of th.) of 6-chloro-2-mercaptobenzoxazole having a melting point of 222°–224° C. were obtained.

If desired, the potassium mercaptide obtained in the first step can be used directly for further reactions, for example with chlorine.

What is claimed is:

1. A process for the preparation of 5- and 6-halo-2-mercaptobenzoxazoles or the sodium and potassium salts thereof, as a product, which comprises reacting, as one reactant, the corresponding 4- or 5-halo-2-aminophenols with sodium or potassium lower alkyl xanthates, as the other reactant, in a aromatic or aqueous dispersion in which a heterogeneous phase is present of one of the reactants or where the heterocyclic product is also in a heterogeneous phase.

2. The process as claimed in claim 1, which comprises carrying out the reaction in an aromatic hydrocarbon.

3. The process as claimed in claim 2, in which the aromatic hydrocarbon is chlorobenzene or dichlorobenzene.

4. The process as claimed in claim 1, which comprises carrying out the reaction in aqueous suspension.

5. The process as claimed in claim 1, which comprises using industrial-grade xanthates as starting materials for the reaction.

* * * * *